(12) United States Patent
Leeflang et al.

(10) Patent No.: US 6,635,070 B2
(45) Date of Patent: Oct. 21, 2003

(54) APPARATUS AND METHODS FOR CAPTURING PARTICULATE MATERIAL WITHIN BLOOD VESSELS

(75) Inventors: Stephen Leeflang, Stanford, CA (US); Denise DeMarais, San Jose, CA (US); Michael Evans, Palo Alto, CA (US)

(73) Assignee: Bacchus Vascular, Inc., Santa Clara, CA (US)

( * ) Notice: Subject to any disclaimer, the term of this patent is extended or adjusted under 35 U.S.C. 154(b) by 0 days.

(21) Appl. No.: 09/862,174

(22) Filed: May 21, 2001

(65) Prior Publication Data

US 2002/0173819 A1 Nov. 21, 2002

(51) Int. Cl.$^7$ .............................................. A61M 29/00
(52) U.S. Cl. ....................................................... 606/200
(58) Field of Search ................................ 606/113, 114, 606/191, 194, 195, 198, 200

(56) References Cited

U.S. PATENT DOCUMENTS

| | | |
|---|---|---|
| 3,996,938 A | 12/1976 | Clark, III |
| 4,425,908 A | 1/1984 | Simon |
| 4,590,938 A | 5/1986 | Segura et al. |
| 4,619,246 A | 10/1986 | Molgaard-Nielsen et al. |
| 4,706,671 A | 11/1987 | Weinrib |
| 4,723,549 A | 2/1988 | Wholey et al. |
| 4,728,319 A | 3/1988 | Masch |
| 4,790,812 A * | 12/1988 | Hawkins et al. .............. 604/22 |
| 4,794,928 A | 1/1989 | Kletschka |
| 4,873,978 A | 10/1989 | Ginsburg |
| 4,926,858 A | 5/1990 | Gifford, III et al. |
| 4,950,238 A | 8/1990 | Sullivan |
| 5,011,488 A | 4/1991 | Ginsburg |
| 5,053,008 A | 10/1991 | Bajaj |
| 5,071,407 A | 12/1991 | Termin et al. |
| 5,100,423 A | 3/1992 | Fearnot |
| 5,108,419 A | 4/1992 | Reger et al. |
| 5,152,777 A | 10/1992 | Goldberg et al. |

(List continued on next page.)

FOREIGN PATENT DOCUMENTS

| | | |
|---|---|---|
| EP | 0737450 A1 | 10/1996 |
| EP | 0934729 A1 | 8/1999 |
| WO | WO 98/39046 A1 | 9/1998 |
| WO | WO 00/29045 A1 | 5/2000 |

OTHER PUBLICATIONS

PCT Publication No. WO 97/42879, "Aortic Occluder with Associated Filter and Methods of Use During Cardiac Surgery", Nov. 20, 1997.
PCT Publication No. WO 98/24377, "Cerebral Protection During Carotid Endarterectomy and Downstream Vascular Protection During Other Surgeries", Jun. 11, 1998.

(List continued on next page.)

Primary Examiner—David O. Reip
Assistant Examiner—Vi X Nguyen
(74) Attorney, Agent, or Firm—Townsend and Townsend and Crew LLP

(57) ABSTRACT

An apparatus includes a jet housing including an inlet and an outlet, and a nozzle within the jet housing for injecting fluid towards the outlet. A filter element is disposed on the inlet, the filter element including openings for preventing particulate larger than a predetermined size from entering the inlet. The jet housing is positioned within a blood vessel, and fluid is injected from the nozzle towards the outlet to create a vacuum at the inlet, thereby causing fluid downstream of the outlet to flow retrograde through the vessel around the jet housing into the inlet. The filter element prevents particulate from entering the inlet, thereby effectively capturing the particulate, which may be aspirated. Alternatively, a filter element is used to filter particulate during a procedure. The filter element everts from a tubular to an everted configuration for capturing particulate.

10 Claims, 8 Drawing Sheets

U.S. PATENT DOCUMENTS

| | | | |
|---|---|---|---|
| 5,190,546 A | 3/1993 | Jervis | |
| 5,300,022 A | 4/1994 | Klapper et al. | |
| 5,329,942 A | 7/1994 | Gunther et al. | |
| 5,376,100 A | 12/1994 | Lefebvre | |
| 5,415,630 A | 5/1995 | Gory et al. | |
| 5,421,832 A | 6/1995 | Lefebvre | |
| 5,549,626 A * | 8/1996 | Miller et al. | 606/200 |
| 5,634,942 A | 6/1997 | Chevillon et al. | |
| 5,695,519 A | 12/1997 | Summers et al. | |
| 5,814,064 A | 9/1998 | Daniel et al. | |
| 5,827,324 A | 10/1998 | Cassell et al. | |
| 5,833,644 A | 11/1998 | Zadno-Azizi et al. | |
| 5,846,260 A | 12/1998 | Maahs | |
| 5,876,367 A | 3/1999 | Kaganov et al. | |
| 5,910,154 A * | 6/1999 | Tsugita et al. | 606/200 |
| 5,911,734 A | 6/1999 | Tsugita et al. | |
| 5,947,988 A | 9/1999 | Smith | |
| 5,997,562 A | 12/1999 | Zadno-Azizi et al. | |
| 6,001,118 A | 12/1999 | Daniel et al. | |
| 6,007,557 A | 12/1999 | Ambrisco et al. | |
| 6,022,336 A | 2/2000 | Zadno-Azizi et al. | |
| 6,050,972 A | 4/2000 | Zadno-Azizi et al. | |
| 6,053,932 A | 4/2000 | Daniel et al. | |
| 6,068,623 A | 5/2000 | Zadno-Azizi et al. | |
| 6,074,357 A | 6/2000 | Kaganov et al. | |
| 6,117,124 A | 9/2000 | Parodi | |
| 6,123,115 A | 9/2000 | Greenhalgh | |
| 6,136,016 A * | 10/2000 | Barbut et al. | 606/200 |
| 6,146,404 A | 11/2000 | Kim et al. | |
| 6,152,909 A | 11/2000 | Bagaoisan et al. | |
| 6,152,946 A | 11/2000 | Broome et al. | |
| 6,156,054 A | 12/2000 | Zadno-Azizi et al. | |
| 6,179,860 B1 | 1/2001 | Fulton, III et al. | |
| 6,221,006 B1 | 4/2001 | Dubrul et al. | |
| 6,258,115 B1 | 7/2001 | Dubrul | |
| 6,346,116 B1 * | 2/2002 | Brooks et al. | 606/200 |
| 6,361,545 B1 * | 3/2002 | Macoviak et al. | 606/200 |
| 6,371,971 B1 * | 4/2002 | Tsugita et al. | 606/200 |
| 6,468,291 B2 * | 10/2002 | Bates et al. | 606/200 |

OTHER PUBLICATIONS

PCT Publication No. WO 98/33443, "Vascular Filter", Aug. 6, 1998.

PCT Publication No. WO 98/39053, "Distal Protection Device and Method", Sep. 11, 1998.

PCT Publication No. WO 98/46297, Cannula with Associated Filter and Methods of Use During Cardiac Surgery Oct. 22, 1998.

PCT Publication No. WO 98/47447, "Bifurcated Stent and distal Protection System", Oct. 29, 1998.

PCT Publication No. WO 98/50103, "Percutaneous Catheter and Guidewire Having Filter and Medical Device Deployment Capabilities", Nov. 12, 1998.

PCT Publication No. WO 99/16382, "Perfusion Filter Catheter", Apr. 8, 1999.

PCT Publication No. WO 99/16362, "Mechanical Clot Treatment Device with Distal Filter", Apr. 8, 1999.

PCT Publication No. WO 99/22673, "Temporary Vascular Filter Guide Wire", May 14, 1999.

PCT Publication No. WO 99/23976, "An Embolic Protection Device", May 20, 1999.

PCT Publication No. WO 99/44542, "Distal Protection Device and Method", Sep. 10, 1999.

PCT Publication No. WO 00/16705, "Vascular Filter System", Mar. 30, 2000.

PCT Publication No. WO 00/50113, "Balloon Catheter with Axial Felxibiolity", Aug. 31, 2000.

PCT Publication No. WO 00/54673, "Apparatus for Containing and Removing Occlusions in the Carotid Arteries", Sep. 21, 2000.

PCT Publication No. WO 00/56245, "Body Vessel Filter", Sep. 28, 2000.

PCT Publication No. WO 00/56391, "Device and Method of Guide Wire Balloon Inflation and Deflation to Prevent Cerebral Embolization During Carotid Stenting", Sep. 28, 2000.

Certified Copy of PCT/US98/08194 Provisional Application Serial No. 60/044,163 entitled "Vascular Stent for Cerebral Protection and Method", Filed Aug. 23, 1997.

Richard S. Kusleika, et al., PCT Publication No. WO 01/15629 A1 entitled, "Slideable Vascular Filter", Mar. 8, 2001.

Richard S. Kusleika, et al., PCT Publication No. WO 01/21100 A1, entitled "Temporary Vascular Filter", Mar. 29, 2001.

* cited by examiner

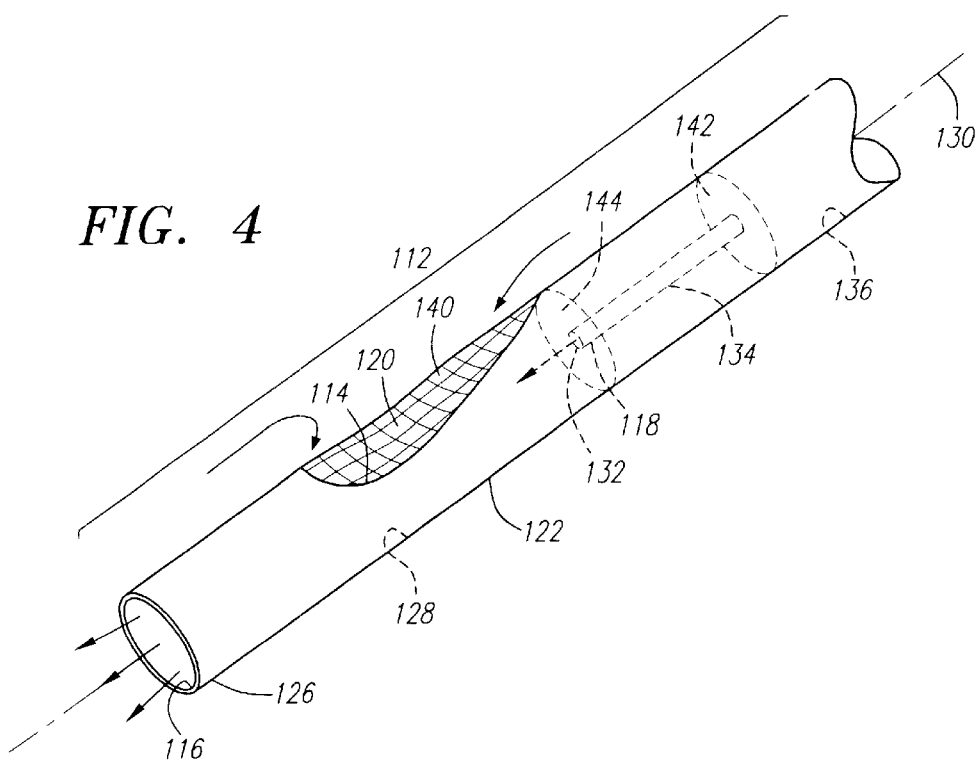
FIG. 4
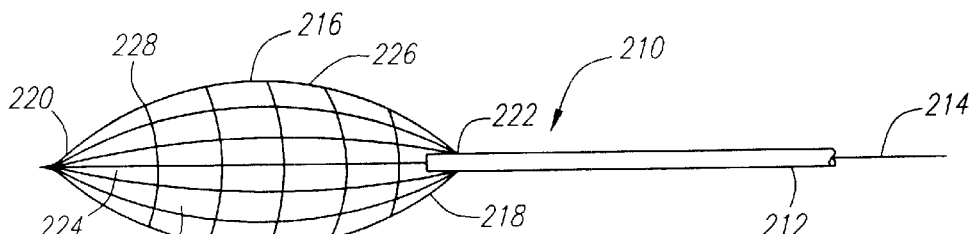
FIG. 5A
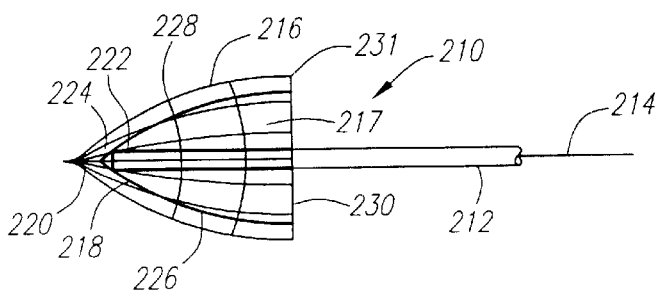
FIG. 5B
FIG. 5C

APPARATUS AND METHODS FOR CAPTURING PARTICULATE MATERIAL WITHIN BLOOD VESSELS

FIELD OF THE INVENTION

The present invention relates generally to apparatus and methods for capturing particulate material within a blood vessel or other body lumen, and more particularly to apparatus and methods for capturing and/or removing particulate material, such as thrombus or other occlusive material, released or removed from a treatment site, e.g., an occlusion, within a blood vessel.

BACKGROUND

A number of endovascular procedures are presently performed on patients with atherosclerotic disease and the like to treat stenoses, occlusions, lesions, or other regions within the patient's blood vessels, such as within the coronary, carotid or cerebral arteries. For example, an angioplasty procedure may be used to dilate a stenosis, or a thrombectomy or atherectomy may be performed to open severely occluded regions. A stent or other prosthesis may be implanted to retain patency of a vessel, either alone or in conjunction with these procedures.

One of the problems with these procedures, however, is that particulate, e.g., thrombus, atheroma, or other embolic or occlusive material may be released from the wall of the vessel during the procedure. If such particulate travel downstream, they may become lodged or otherwise harm the patient. For example, ischemic stroke may occur when such emboli are released in the carotid or cerebral arteries and travel to the patient's brain.

To prevent or minimize damage from emboli, vascular filters have been suggested that are generally mounted on a device, such as a catheter, a guidewire, or a sheath. These devices may be introduced within a blood vessel downstream of a location being treated, and the filter on the device deployed across the vessel to capture embolic material released during a procedure, such as one of the procedures above. Upon completion of the procedure, the filter may be collapsed, trapping emboli therein, and then the device may be removed from the patient.

Alternatively, procedures have been suggested that involve deploying a balloon or other occlusive device downstream from a treatment site. The balloon may be expanded to prevent blood flow, thereby trapping any emboli released during the procedure. An aspirating catheter may be advanced into the vessel upstream of the balloon, and vacuum applied to remove the emboli before deflating and removing the balloon. Because this procedure completely blocks the vessel from fluid flow, the balloon may not be inflated for extended periods of time without depriving locations downstream of blood supply, which may be harmful to the patient.

Implantable filter devices have also been suggested that may be deployed, expanded and released within vessels, such as vena cava filters. These filter devices may not be recovered, or may it remain within the vessel for extended periods of time, where they may eventually become occluded with thrombus, clots, emboli and the like, which may harm the patient.

Accordingly, apparatus and methods for capturing and/or removing particulate material, such as thrombus or occlusive material, within a blood vessel would be considered useful.

SUMMARY OF THE INVENTION

The present invention is directed to apparatus and methods for capturing particulate material within a blood vessel or other body lumen, and more particularly to apparatus and methods for capturing and/or removing particulate material, such as thrombus or other occlusive material, released or removed from a treatment site, e.g., an occlusion, within a blood vessel.

In accordance with one aspect of the present invention, an apparatus is provided that includes a tubular member or jet housing including an inlet and an outlet. The tubular member has a cross-section substantially smaller than a cross-section of a body lumen such that the tubular member may be introduced into a body lumen generally parallel to a natural direction of fluid flow within the body lumen such that the outlet is oriented downstream of the inlet within the body lumen. A nozzle is disposed within the tubular member and oriented to inject fluid towards the outlet for generating a vacuum at the inlet.

A filter element is disposed on the inlet, the filter element including a plurality of openings having a predetermined maximum size for preventing particulate larger than the maximum size from entering the inlet of the tubular member. In one embodiment, the filter element may include a filter mesh covering the inlet, the plurality of openings including a plurality of pores in the filter mesh. In a second embodiment, the filter element may be a tubular body extending from the inlet, the tubular body including the plurality of openings in its wall.

In addition, the apparatus may include an aspirating element for removing particulate captured by the filter element. For example, the aspirating element may be a catheter that is advanceable over the tubular member, the catheter including a lumen for removing particulate captured by the filter element.

In accordance with another aspect of the present invention, a method is provided for capturing particulate within a body lumen of a patient. A tubular member may be positioned within a body lumen, the tubular member including an inlet and an outlet, the inlet being located upstream of the outlet within the body lumen. A jet of fluid may be injected from within the tubular member towards the outlet, the jet creating a vacuum at the inlet, the vacuum being sufficient to cause fluid downstream of the outlet to flow retrograde through the body lumen around at least a portion of the tubular member into the inlet. A filter element may be provided on the inlet, the filter element including a plurality of openings having a predetermined maximum size for preventing particulate larger than the maximum size from entering the inlet, thereby capturing the particulate at a location upstream of the outlet of the tubular member.

The captured particulate may be removed from the body lumen. For example, the particulate may be aspirated from the location upstream of the outlet, e.g., by advancing a distal end of a catheter into the body lumen to aspirate the particulate into the catheter.

The method may be performed along with one or more other interventional procedures at a location upstream from the tubular member, the procedure releasing material from a wall of the body lumen. For example, the procedure may include diagnostic and/or therapeutic interventions, such as thrombectomy, atherectomy, angioplasty, thrombolysis, endarterectomy, and/or stent delivery, such as coated stent delivery, drug eluting stent delivery, and the like.

In accordance with yet another aspect of the present invention, an apparatus is provided that includes a first elongate member including a distal portion having a size for introduction into a body lumen and defining a longitudinal axis. A tubular filter element is also provided having first and second ends adjacent first and second respective portions of the filter element. The first end is substantially fixed to the distal portion of the first elongate member, and the second end is movable axially with respect to the distal portion of the first elongate member towards the first end to evert the filter element. Preferably, the filter element is biased to assume a predetermined configuration programmed into a shape memory of the filter element material when the filter element is everted, the second portion being located substantially within the first portion in the predetermined configuration.

In a preferred embodiment, the apparatus also includes a second elongate member including a distal portion to which the second end of the filter element is fixed. The second elongate member is slidable along the first elongate member for moving the first and second ends of the filter element towards one another to cause the filter element to evert. Preferably, the second elongate member includes a lumen through which the first elongate member is slidably received.

Similar to the previous embodiment, the apparatus may also include an aspirating element having an inlet that may be disposed within an interior of the filter element in the predetermined configuration.

In one embodiment, the filter element may define a space between the first and second portions in the predetermined configuration, and the first portion may include pores therein that are substantially smaller than pores in the second portion. The filter element may include one or more struts extending from the second portion of the filter element to a distal end of a second elongate member slidably disposed on the first elongate member.

Preferably, the filter element is biased to assume an expanded tubular configuration when the second portion of the filter element is removed from within the first portion.

To manufacture a filter element in accordance with the present invention, an elongate tubular mesh or braid may be provided having first and second ends, and first and second portions adjacent the first and second ends, respectively. The tubular mesh may be shaped into an everted configuration in which the second portion is disposed concentrically within the first portion. The tubular mesh may then be heated to a predetermined temperature to program the everted configuration into a shape memory of the tubular mesh. After heating, the second portion may be removed from within the first portion to dispose the tubular mesh in a generally tubular configuration, the tubular mesh maintaining the tubular configuration in a relaxed state.

First and second elongate members, e.g., coaxial guidewires, may be attached to the first and second ends of the tubular mesh, respectively. The first and second elongate members may be movable axially with respect to one another to move the first and second ends towards and away from one another.

The filter element may be used to capture particulate within a body lumen, e.g., a blood vessel, at a location downstream of a treatment site. The distal portion of the elongate member may be advanced to a location within a body lumen downstream of a treatment site, the tubular filter element being disposed in a radially compressed configuration. The first and second ends of the filter element may be directed towards one another, whereupon the filter element may automatically evert such that the second portion is located substantially within the first portion, and an intermediate portion between the first and second portions expands to engage a wall of the body lumen.

Particulate passing along the body lumen may be captured within the everted filter element, and the particulate captured within the filter element may be aspirated. The first and second ends of the filter element may then be moved away from one another to remove the second portion from within the first portion. The filter element may be collapsed radially inward, and the filter element may be removed from the body lumen.

Other objects and features of the present invention will become apparent from consideration of the following description taken in conjunction with the accompanying drawings.

BRIEF DESCRIPTION OF THE DRAWINGS

FIG. 4 is a perspective view of a second preferred embodiment of an apparatus for hydro-dynamically capturing particulate within a blood vessel, in accordance with the present invention.

FIGS. 5A–5C are side views of a preferred embodiment of an everting filter apparatus for capturing particulate within a blood vessel, in accordance with the present invention.

DETAILED DESCRIPTION OF THE PREFERRED EMBODIMENTS

Figure 1A:
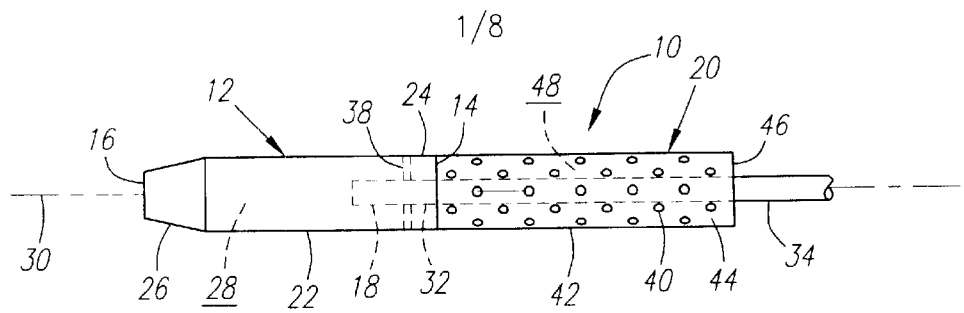
FIG. 1A is a side view of a first preferred embodiment of an apparatus for hydro-dynamically capturing particulate within a blood vessel, in accordance with the present invention.
Figure 1B:
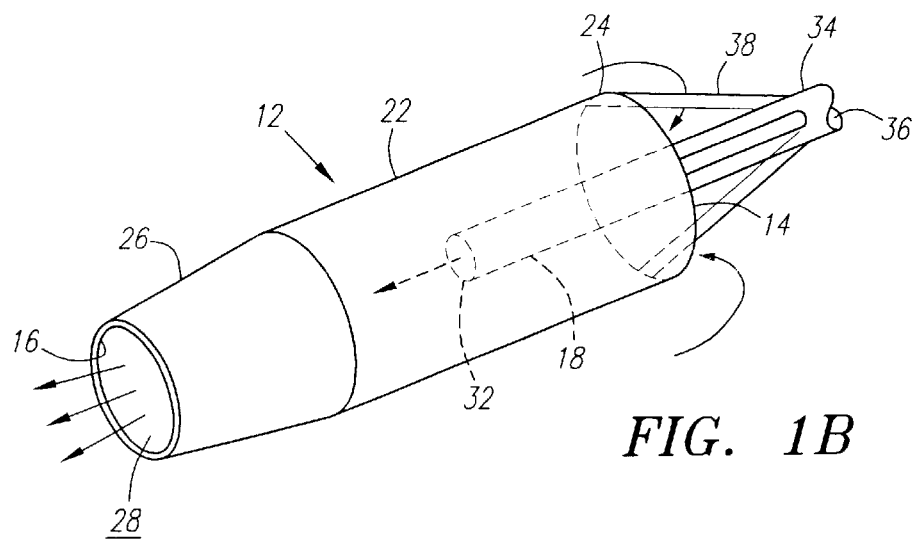
FIG. 1B is a perspective view of a jet housing for use with the apparatus of FIG. 1.

Turning now to the drawings, FIGS. 1A and 1B show a first preferred embodiment of an apparatus 10 for capturing particulate, such as thrombus or occlusive material within a blood vessel or other body lumen, in accordance with the present invention. Generally, the apparatus 10 includes a jet housing 12 including an inlet 14 and an outlet 16, a jet nozzle 18 disposed within the jet housing 12, and a filter element 20 on the inlet 14 of the jet housing 12.

The jet housing 12 has a cross-section substantially smaller than a cross-section of a blood vessel or other body lumen within which the jet housing 12 may be introduced, as described further below. For example, the jet housing 12 may be a tubular segment 22 having a diameter of between about one and five millimeters (1–5 mm) formed from metals, such as stainless steel or Nitinol, or polymers, such as polyamide, ABS, PEBAX, or PTFE. Preferably, the tubular segment 22 includes a proximal end 24 and a distal end 26 and a lumen 28 extending therebetween, thereby defining a longitudinal axis 30. The distal end 26 may include a tapered tip, as shown, and/or the distal end 26 may be flexible or otherwise substantially atraumatic, e.g., to facilitate advancement through a patient's vasculature. Optionally, one or more centering members (not shown) may be provided that extend radially outwardly from the jet housing 12, e.g., to maintain the jet housing 12 generally concentrically within a body lumen.

The jet nozzle 18 is disposed within the jet housing 12 and is oriented to inject fluid towards the outlet 16 for generating a vacuum at the inlet 14. Preferably, the jet nozzle 18 includes an open distal end 32 of an elongate tubular member 34, e.g., a catheter. The tubular member 34 includes a proximal end (not shown) that may be disposed outside a patient's body and a lumen 36 that extends between the proximal end and the distal end 32. The proximal end may be coupled to a source of high pressure fluid (not shown), e.g., thrombolytics, or other therapeutic agents, blood and/or heparinized saline. For example, the source may be a pump configured for delivering fluid at a pressure between about one hundred and fifteen thousand pounds per square inch (100–15,000 psi), and/or at a flow rate of up to about one hundred cubic centimeters per minute (100 cc/minute).

The distal end 32 has a cross-section that is substantially smaller than the cross-section of the jet housing 12. For example, the distal end may have a diameter of up to two millimeters (2 mm). The jet nozzle 18 is generally fixed relative to the jet housing 12, e.g., connected by one or more struts 38.

The filter element 20 is attached to or otherwise disposed adjacent the inlet 14 of the jet housing 12. The filter element 20 includes one or more pores, holes, or other openings 40 having a predetermined maximum size for preventing particulate larger than the maximum size from entering the inlet 14 of the jet housing 12. In the embodiment shown, the filter element 20 is a tubular body 42 including a plurality of holes 40 in its wall 44. A proximal end 46 of the filter element 20 may be tapered and/or closed to prevent particulate larger than the maximum size from entering an interior space 48 of the tubular body 42. The interior space 48 communicates directly with the inlet 14 of the jet housing 12, thereby providing a fluid path from the holes 40 through the interior space 48 and the inlet 14 of the jet housing 12 to the outlet 16.

Preferably, the tubular body 42 is attached to or otherwise extends from the proximal end 24 of the jet housing 12, e.g., substantially parallel to the longitudinal axis 30. The openings 40 may be distributed along the tubular body 42 in a desired pattern, e.g., becoming progressively larger or smaller along the length of the tubular body 42. The tubular body 42 may be formed from metals, such as stainless steel or Nitinol, or polymers, such as polyamide, ABS, PEBAX or PTFE, such that the tubular body 42 is sufficiently flexible to facilitate introduction through tortuous anatomy.

Figure 2A:
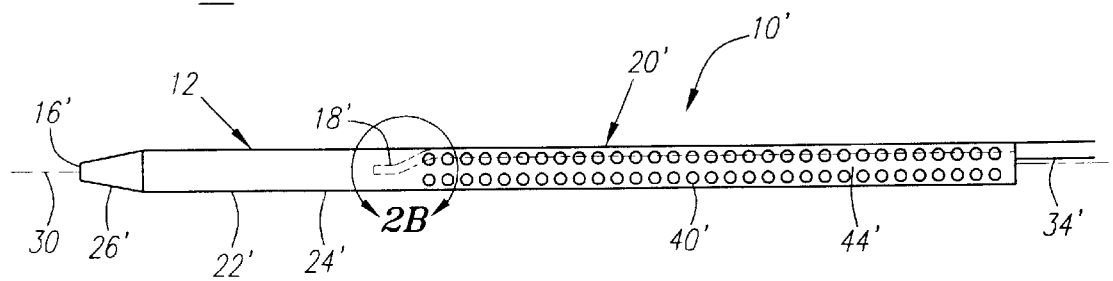
FIG. 2A is a side view of an alternative embodiment of an apparatus for hydro-dynamically capturing particulate within a blood vessel, in accordance with the present invention.
Figure 2B:
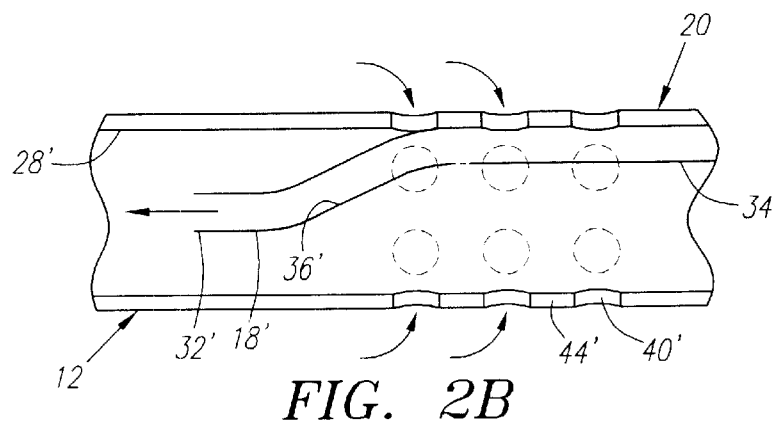
FIG. 2B is a detail of the apparatus of FIG. 2A.

Alternatively, as shown in FIGS. 2A and 2B, the filter element 20' may be a direct extension of the jet housing 12', including holes 40' in the wall 44'. The tubular member 34' may extend along an inner surface of the wall 44', and the jet nozzle 18' may extend from the inner surface to a concentric location distal to the distal-most holes 40'. In a further alternative, the filter element 20 may be a mesh, e.g., a braid of fibers or a sheet of material including perforations or other pores formed therein (not shown) that may cover or extend from the inlet 14. The pore size of the mesh may prevent particulate larger than the predetermined maximum size from passing through the mesh into the inlet 14.

Figure 3A:
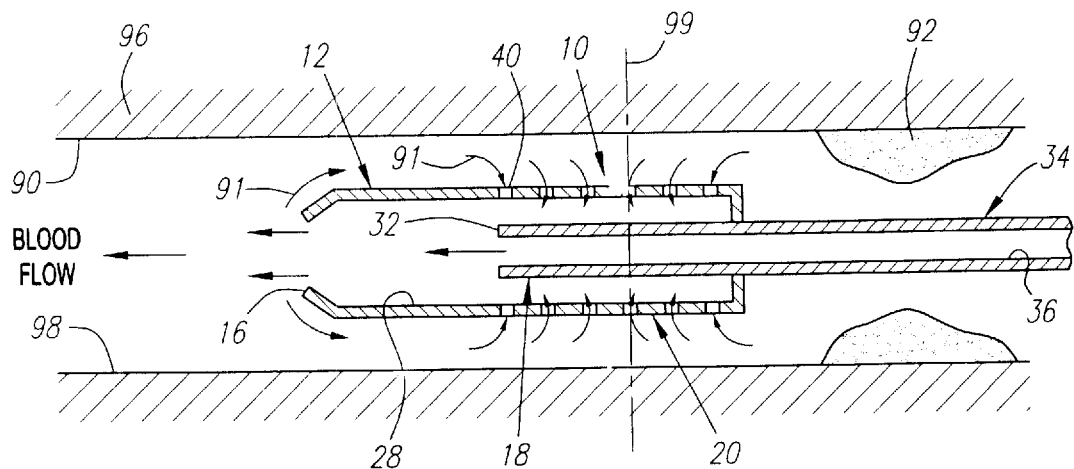
FIGS. 3A–3C are cross-sectional views of a blood vessel, showing a method for capturing particulate, in accordance with the present invention.
Figure 3B:
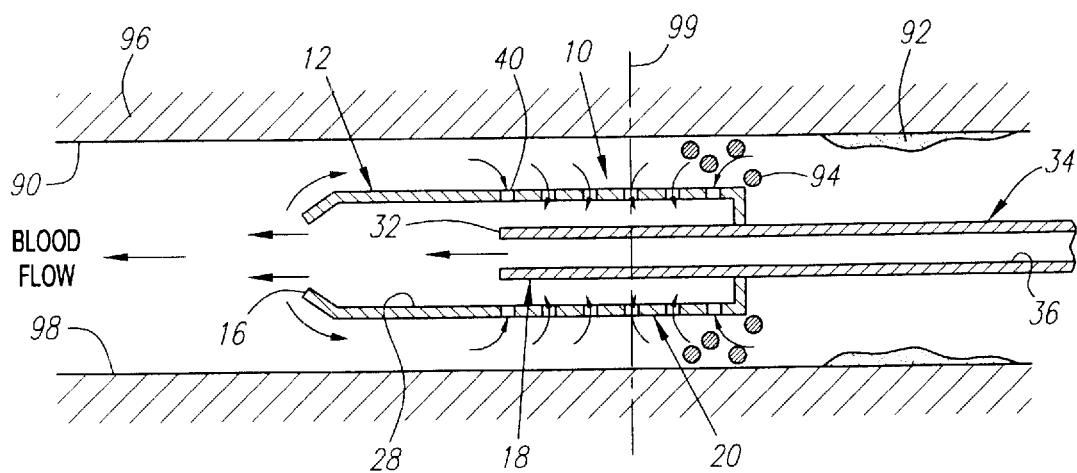
Figure 3C:
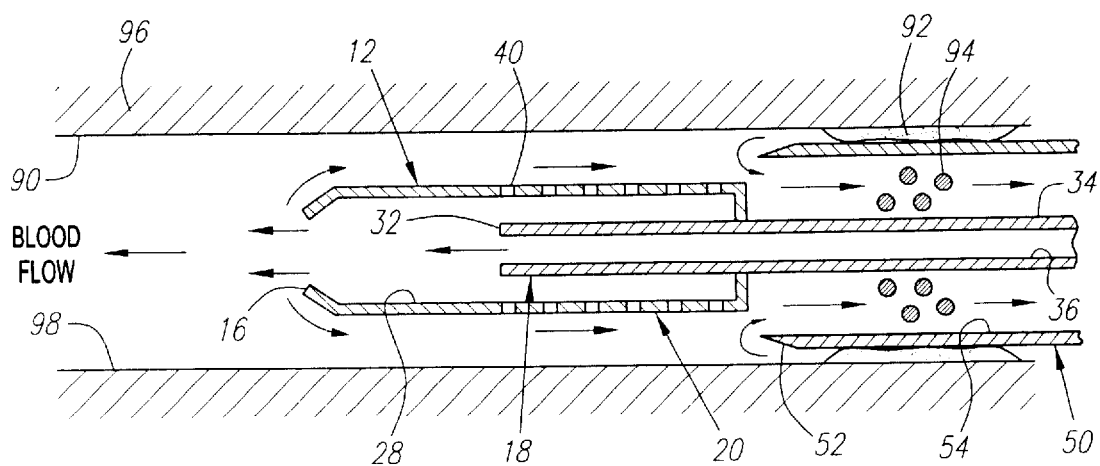

Turning to FIGS. 3A–3C, the apparatus 10 may be used to capture particulate, e.g., thrombus and/or occlusive material 94, passing along a predetermined location within a blood vessel 90 or other body lumen. The apparatus 10 is first advanced into the vessel 90 until the jet housing 12 is disposed downstream (with respect to natural flow within the vessel 90) of a treatment site, such as occlusion 92. For example, the apparatus 10 may be introduced into a patient's vasculature from a percutaneous entry site, e.g., at a peripheral vessel (not shown), such as a femoral or carotid artery using conventional methods, and advanced into the vessel 90.

Preferably, the apparatus 10 is advanced over a guidewire (not shown) that may have been previously placed within the vessel 90 from the entry site. Initially, outside the patient's body, the guidewire may be backloaded through the outlet 16 and through the lumen 36 of the tubular member 34, or through a separate guidewire lumen (not shown). The distal end 26 of the jet housing 12 may then be directed into the entry site and through the patient's vasculature to the vessel 90. Alternatively, the apparatus 10 itself may be a guidewire. In a further alternative, the apparatus 10 may be disposed within a distal end of a sheath or guide catheter (not shown), the distal end of the sheath may be advanced into the vessel 90, and the sheath may then be withdrawn to expose the jet housing 12 within the vessel 90.

As shown in FIG. 3A, the apparatus 10 is positioned in an "antegrade" manner, i.e., the apparatus 10 is advanced along the vessel 90 in the same direction as natural blood flow. The jet housing 12 may be directed through the treatment site 92 and positioned a predetermined distance downstream from the occlusion 92, e.g., such that the filter element 18 is located distally from the occlusion 92. Thus, the outlet 16 and the jet nozzle 18 are both oriented downstream within the vessel 90.

In an alternative embodiment, the apparatus 10 may be introduced in a "retrograde" manner, i.e., the apparatus 10 may be advanced against the direction of natural blood flow into the vessel 90 downstream from the occlusion 92 (not shown). In this embodiment, the jet nozzle 18 may include a bend or "J" tip (not shown) to orient the fluid flow from the jet nozzle 18 downstream within the vessel 90. In this embodiment, the tubular member 34 terminating in the jet nozzle 18 may pass through the outlet 16 into the jet housing 12 (rather than through the inlet, as shown). The filter element (not shown) may still extend towards the occlusion 92 from the inlet 14 of the jet housing 12, i.e., opposite the tubular member.

Once the apparatus 10 is positioned at a desired location, fluid, e.g., thrombolytics, or other therapeutic agents, blood, and/or heparinized saline, may be injected from the jet nozzle 18 in a downstream direction within the jet housing 12, i.e., towards the outlet 16. Preferably, the fluid is delivered at a relatively high pressure, e.g., between about one hundred and fifteen thousand pounds per square inch (100–15,000 psi), such that the pressure causes the fluid to leave the open distal end 32 at a relatively high velocity. This causes fluid to exit the outlet 16 of the jet housing 12 at a relatively high flow rate compared to a natural flow rate for the vessel 90. This action generates a vacuum or relatively low pressure at the inlet 14, causing fluid to flow into the inlet 14 at a substantially increased flow rate. Preferably, the inlet flow rate increases to such a degree that the vessel 90 upstream of the jet housing 12 cannot supply sufficient fluid, thereby causing fluid to flow retrograde from the outlet 16 around the jet housing 12 and into the inlet 14, as represented by exemplary arrows 91.

With the filter element 20 extending from the inlet 14 of the jet housing 12, fluid must pass through the holes 40 to enter the inlet 14. The fluid may then pass through the lumen 28 within the jet housing 12 and from the outlet 16. Depending upon the flow parameters of the fluid injected via the jet nozzle 18 (e.g., pressure and/or flow rate), fluid flow around the apparatus 10 reaches a dynamic equilibrium. While some fluid may continue to flow naturally from upstream of the vessel 90, fluid also flows retrograde around the jet housing 12, thereby providing sufficient fluid to satisfy the required flow rate through the jet housing 12 and out the outlet 16. Thus, the balance of these two flows (natural antegrade and jet-induced retrograde) creates a dead zone or balance point 99 at which no fluid may flow downstream and no fluid may flow upstream.

It will be appreciated by those skilled in the art that the various dimensional and/or operational parameters of the apparatus 10 may be used to obtain a desired predetermined dead zone 99. For example, the ratio of the cross-sections or diameters of the jet housing 12 and the vessel 90, the pressure of the fluid injected via the jet nozzle 18, and the like may be selected to create a desired flow pattern, e.g., using Bernoulli's equation or other fluid mechanics principles that are well known to those skilled in the art.

A procedure may then be performed at the treatment site 92, which may involve the release of particulate or other material 94 from the wall 98 of the vessel 90 (either intentionally or unintentionally). For example, a device (not shown) may be introduced into the lumen 90 to remove unwanted tissue from the treatment site 92, such as thrombus, atheroma, or other occlusive material extending from the wall 98 of the vessel 90. Devices that may used to remove such unwanted tissue are disclosed in co-pending application Ser. Nos. 09/005,217, filed Jan. 9, 1998, 09/540, 162, filed Feb. 15, 2000, 09/640,499 filed Aug. 16, 2000, 09/704,967 filed Nov. 1, 2000, 09/454,517, filed Dec. 6, 1999, 09/590,915, filed Jun. 9, 2000, 09/491f401 filed Jan. 25,2000, 09/820,301 filed Mar. 27, 2001, 09/823,652, filed Mar. 30, 2001, 60/274,104 filed Mar. 7, 2001, and 09/820, 084 filed Mar. 27, 2001. The disclosure of these applications, and any references cited therein, are expressly incorporated herein by reference. Alternatively, other procedures may be performed at the treatment site 92, such as angioplasty, stent delivery, atherectomy, thrombectomy, and the like.

During the procedure, particulate 94 released from the treatment site 92 may travel downstream within the vessel 90 until it approaches the jet housing 12. Because of the dead zone 99, the particulate 94 cannot pass distally beyond the jet housing 12 without passing through the lumen 28 of the jet housing 12. The filter element 20 prevents particulate 94 larger than the maximum size of the holes 40 from entering the inlet 14. Thus, the holes 40 may allow fluid to pass freely into the inlet 14, through the lumen 28, and from the outlet 16 back into the vessel 90, where it may travel downstream and maintain substantially normal blood flow. Particulate 94, however, remains captured adjacent the filter element 20, preventing the particulate 94 from traveling downstream where it may cause substantial harm to the patient, as shown in FIG. 3B.

The particulate 94 generally may tend to flow downstream until they build up proximal to the dead zone 99. Consequently, the distal-most holes 40 in the filter element 20 may become occluded during the procedure. To allow continued flow, the filter element 20 preferably includes sets of holes 40 disposed along the filter element 20, as best seen in FIG. 1. If the distal-most holes 40 become occluded, fluid may continue to pass through the more proximal holes 40. Thus, if it is known that the procedure may take a substantial time and/or may involve releasing a significant amount of particulate, a filter element 20 having a longer length may be provided to ensure that at least some of the holes 40 remain substantially open in order to allow fluid flow to continue.

Upon completion of the procedure, the particulate 94 may be removed from the vessel 90. For example, a distal end 52 of an aspirating catheter 50 may be advanced into the vessel 90 proximal to the dead zone 99. Preferably, the aspirating catheter 50 has a lumen 54 that is sufficiently large such that the catheter 50 may be advanced over the tubular member 34 and/or over the filter element 20. A source of vacuum may be coupled to a proximal end (not shown) of the aspirating catheter 50, and the distal end 52 may be advanced into sufficiently close proximity to the dead zone 99 to aspirate the particulate 94 into the aspirating catheter 50, as shown in FIG. 3C.

For extensive procedures, an aspirating catheter 50 may be advanced periodically over the tubular member 34 to prevent excessive build-up of particulate 94, which may substantially occlude the filter element 20 and prevent fluid flow from continuing. In an alternative embodiment, the aspirating catheter 50 may be advanced independently into the vessel 90, e.g., over a separate guidewire.

Turning to FIG. 4, another embodiment of an apparatus 110 is shown that may be used to capture particulate, similar to the embodiment described above. The apparatus 110 includes an elongate tubular member 122, including a proximal end (not shown), and a distal portion 112 terminating in a distal end 126. The tubular member 122 has a cross-section that is smaller than a cross-section of a blood vessel or other lumen within which the tubular member 122 is advanced, similar to the jet housing described above.

A proximal lumen 136 extends between the proximal end and the distal portion 112, thereby defining a longitudinal axis 130. One or more septum walls 142, 144 are disposed within the tubular member 122 to substantially isolate the proximal lumen 136 from a distal lumen 128 within the distal portion 112. The distal portion 112 of the tubular member 122 includes an outlet 116 in the distal end 126, and an inlet 114 proximal to the outlet 116, e.g., in the wall of the tubular member 122 proximal to the distal end 126. The distal lumen 128 provides a flow path between the inlet 114 and the outlet 116.

The apparatus 110 may also include a filter element 120, e.g., a filter mesh including a plurality of pores or openings 140, that extends over the inlet 114. Alternatively, a plurality of holes (not shown) having a predetermined maximum size may be provided in the wall of the distal portion 112.

A jet nozzle 118 is provided in the tubular member 122 adjacent the inlet 114. Preferably, the jet nozzle 118 is a tubular segment 134 having a cross-section that is substantially smaller than a cross-section of the tubular member 122. The tubular segment 134 extends between proximal and distal septum walls 142, 144 such that a distal opening 132 in the tubular segment 134, defining the jet nozzle 118, communicates with or extends into the distal lumen 128. Thus, the tubular segment 134 defines a flow path from the proximal lumen 136 to the distal lumen 128. If desired, one of the septum walls may be eliminated, although struts or supports may then be needed to provide lateral stability of the tubular segment 134.

During use, the apparatus 110 is advanced into a blood vessel downstream of a treatment site, similar to the embodiment described above. A source of fluid may be connected to the proximal end of the tubular member 122, and fluid may be delivered through the proximal lumen 136. The fluid passes through the tubular segment 134, preferably at a predetermined pressure, and out the jet nozzle 118 into the distal lumen 128, thereby inducing a vacuum at the inlet 114 as the fluid exits the outlet 116. This may create a retrograde flow pattern around the distal portion 112, similar to the flow pattern around the jet housing 12 described above. This flow pattern may generate a dead zone for capturing particulate that are too large to pass through the pores 140 of the filter element 120. Thus, the distal portion 112 behaves substantially similarly to the jet housing 12 described above.

A procedure may be performed upstream from the distal portion 112, as described above, and released thrombus, occlusive material, or other particulate may be captured between the dead zone and the filter element 120. The captured particulate may be aspirated, e.g., by advancing an aspirating catheter over the tubular member 122, or otherwise removed from the vessel. Upon completion of the procedure, the apparatus 110 may also be removed.

Turning to FIGS. 5A–5C, another preferred embodiment of an apparatus 210 is shown for capturing particulate, in accordance with the present invention. Generally, the apparatus 210 includes a pair of substantially flexible guidewires or other elongate members 212, 214, and a tubular filter element 216 having proximal and distal ends 218, 220 attached to respective distal ends 222, 224 of the elongate members 212, 214. The guidewires 212, 214 are slidable relative to one another for directing the filter element 216 between a compressed configuration (FIG. 5A), an expanded configuration (FIG. 5B), and an everted configuration (FIG. 5C), as described further below.

The guidewires 212, 214 are preferably coaxial with one another. The outer guidewire 212 has a lumen therein (not shown) through which the inner guidewire 214 may be inserted, preferably such that the distal end 224 of the inner guidewire 214 extends beyond the distal end 222 of the outer guidewire 212. The inner guidewire 214 is preferably a single strand of wire, although alternatively, it may include one or more strands wound helically around an axial strand. The outer guidewire 212 may be a solid tube, or alternatively, the outer guidewire 212 may include a helically wound strand or multiple braided strands (not shown). In a further alternative, a tubular member, such as a guide catheter or sheath (not shown), may be used instead of the outer guidewire 212. The guidewires 212, 214 may be formed from conventional guidewire materials, e.g., braid-reinforced polymers/composites, stainless steel, Nitinol, or other metals, which may be coated, e.g., with PTFE, to facilitate their sliding relationship.

The filter element 216 includes proximal and distal portions 226, 228 adjacent the proximal and distal ends 218, 220, respectively. The proximal and distal ends 218, 220 may be substantially closed and/or may be secured around the distal ends 222, 224 of the respective guidewires 212, 214. The filter element 216 is a tubular mesh including a plurality of pores, holes, or other openings 217 therethrough having a predetermined maximum size. In a preferred embodiment, the mesh is formed from a plurality of tubular strands that are braided together in a predetermined manner. Alternatively, the tubular mesh may be formed by cutting a hole pattern in a sheet of material and rolling the sheet into a tubular shape.

Preferably, the configuration of the filter element 216 is controlled by sliding the distal ends 222, 224 of the guidewires 212, 214 axially relative to one another. For example, the distal ends 222, 224 may be moved away from one another, thereby subjecting the filter element 216 to tension. This generally causes the mesh to move radially inwards to the compressed configuration shown in FIG. 5A. The first and second ends 222, 224 may be moved towards one another until an expanded configuration, such as that shown in FIG. 5B, is attained. This may define a first relaxed state to which the filter element 216 may be biased to return when free from external forces and before the filter element 216 is everted.

If the first and second ends 222, 224 are moved even further closer together, the filter element 216 may "evert," i.e., the proximal portion 226 may enter and become disposed within the distal portion 228. Preferably, the filter element 216 has a shape memory programmed into the mesh material, such that, as the filter element 216 everts, the proximal portion 226 automatically becomes biased to a predetermined configuration concentrically within the distal portion 228. The filter element 216 defines a cavity 230 in the everted configuration within which particulate (not shown) may be captured. Thus, the filter element 216 may have two configurations to which it is biased, one having an elongated, noneverted shape, and one having an everted shape.

During use, the filter element 216 may be constrained in the compressed configuration of FIG. 5A, e.g., by directing the distal ends 222, 224 of the guidewires 212, 214 away from one another, e.g., preferably by pulling the outer guidewire 212 proximally. The filter element 216 may be directed into a delivery apparatus, e.g., within a distal portion of a catheter or sheath (not shown). The catheter may include an actuator or other locking device (not shown) for securing the guidewires 212, 214 relative to one another, i.e., to maintain the tension causing the filter element 216 to assume the compressed configuration. The catheter may also include an actuator or other locking device for securing the filter element 216 in the everted or other open configuration.

The filter element 216, e.g., within the catheter is advanced to a location within a blood vessel or other body lumen downstream of a treatment site (not shown), similar to the embodiments described above. The filter element 216 may be deployed, e.g., by retracting the distal portion of the overlying catheter. The locking apparatus securing the guidewires 212, 214 may be released, whereupon the filter element 216 may become biased to assume the elongate expanded configuration shown in FIG. 5B. Thus, the proximal and distal ends 218, 220 of the filter element 216 may move partially towards one another, thereby pulling the distal ends 222, 224 of the guidewires 212, 214 closer together. Alternatively, the guidewires 212, 214 may be manipulated to expand the filter element 216.

Once the filter element 216 is disposed at a desired position (which may be adjusted, if necessary, by pulling the outer guidewire 212 to temporarily compress the filter element 216), the first and second ends 218, 220 of the filter element 216 may be directed towards one another. This causes the filter element 216 to automatically evert such that the proximal portion 226 is located substantially within the distal portion 228, as shown in FIG. 5C. An intermediate portion 231 between the first and second portions 226, 228 may expand to substantially engage a wall of the vessel.

A procedure may then be performed upstream of the filter element 216, e.g., at an occlusion, lesion, or other treatment site within the vessel, which may release particulate, as described with respect to the previous embodiments. In a particularly preferred procedure, the filter element 216 is used during a thrombectomy or similar procedure using a shearing and/or vibrating device (not shown), such as those disclosed in the applications incorporated above. For example, the device may include cooperating shearing members (also not shown) that may be disposed within the treatment site, e.g., an occlusion. The filter element 216 may be coupled to the device, e.g., the apparatus 210 may be extended from a lumen within the device and or may be provided on a distal extension of the device. One or more shearing members may be rotated relative to one another to shear or macerate thrombus, occlusive material, and/or other tissue from the treatment site.

Any particulate released during the procedure may travel downstream and become captured within the cavity 230 defined by the filter element 216 in the everted configuration. The pore size of the openings 217 in the filter element 216 may be predetermined to capture only particulate that is large enough to create significant risks to the patient if the particulate were free to travel downstream beyond the filter element 216. For example, a pore size up to three millimeters (3 mm) may be desirable.

At one or more times during the procedure, it may be desirable to aspirate particulate captured within the filter element, e.g., to prevent the cavity 230 from filling and substantially occluding the vessel. An aspirating catheter or other device may be advanced from upstream within the vessel, and a distal end of the catheter may be directed into the cavity 230 and a vacuum created to remove the particulate captured within the filter element 216.

Upon completion of the procedure, the distal ends 222, 224 of the guidewires 212, 214 may be moved away from one another (e.g., by pulling the outer guidewire 212) to move the first and second ends 218, 220 of the filter element 216 away from one another and remove the proximal portion 226 from within the distal portion 228 of the filter element 218. Once in an elongate tubular configuration (e.g., FIG. 5B), the filter element 216 may be collapsed radially inward, e.g., to the compressed configuration (shown in FIG. 5A). A sheath or other device (not shown) may be advanced over the filter element 216, and the filter element 216 may be withdrawn from the vessel and from the patient's body.

Figure 6A:
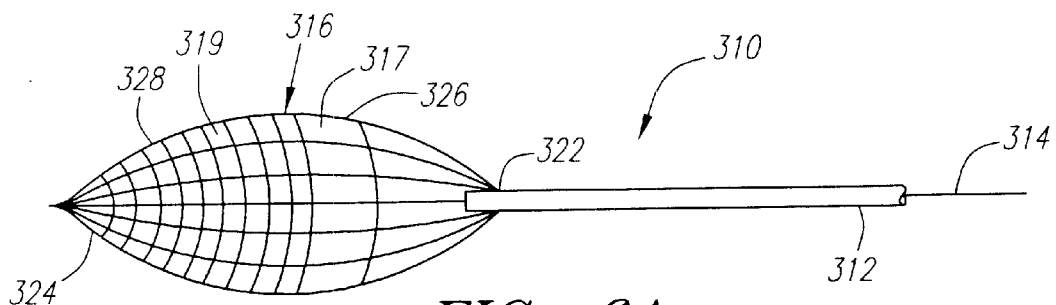
FIGS. 6A and 6B are side views of an alternative embodiment of an everting filter apparatus for capturing particulate within a blood vessel.
Figure 6B:
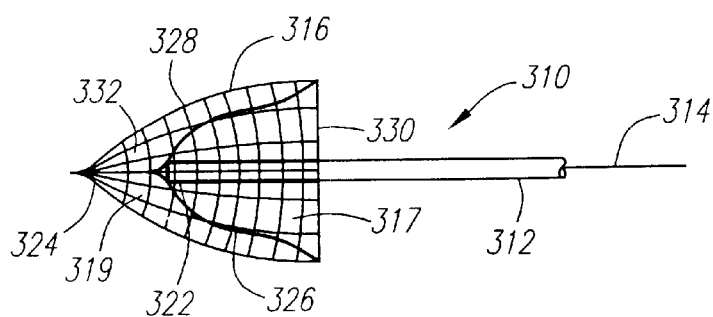

Turning to FIGS. 6A and 6B, an alternative embodiment of a filter element 316 is shown that includes proximal and distal portions 326, 328 having different pore sizes. Preferably, the distal portion 328 has a plurality of openings 319 therein that are substantially smaller than the plurality of openings 317 in the proximal portion 326. When the filter element 316 is everted (FIG. 6B), the proximal portion 326 enters the distal portion 328, and the filter element 316, similar to the embodiment described above. Unlike the previous embodiment, however, in the everted configuration to which the filter element 216 is biased, the filter element 216 preferably defines a space 332 between the proximal and distal portions 326, 328. When particulate enters the cavity 330, particulate smaller than the openings 317 in the proximal portion 326 and larger than the openings 319 in the distal portion 328 may pass through the proximal portion 326 and become captured in the space 332 within the filter element 316.

Figure 7A:
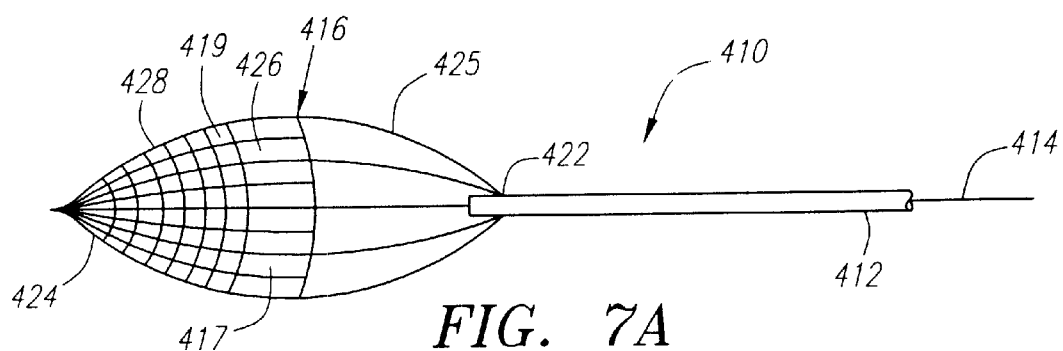
FIGS. 7A and 7B are side views of another alternative embodiment of an everting filter apparatus for capturing particulate within a blood vessel.
Figure 7B:
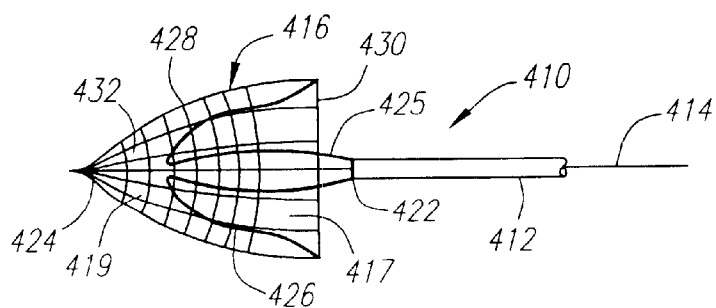

In a further alternative, shown in FIGS. 7A and 7B, a filter element 416 may be provided that includes a proximal portion 425, an intermediate portion 426, and a distal portion 428. The proximal portion 425 may include a plurality of struts for coupling the filter element 416 to an outer guidewire, while the distal portion 428 may be coupled to an inner guidewire 424, similar to the embodiments described above. Alternatively, the proximal portion 425 may simply include relatively large openings to allow particulate to pass through the proximal portion 425. The intermediate portion 426 preferably includes openings 417 defining a pore size that is substantially larger than a pore size of openings 419 in the distal portion 428.

When the filter element 416 is everted, as shown in FIG. 7B, the intermediate portion 426 becomes disposed within the distal portion 428 to define a space 432 within the filter element 416, similar to the previous embodiment. Preferably, the filter element 416 is biased to assume a predetermined everted configuration, such as that shown in FIG. 7B. Similar to the previous embodiment, the filter element 416 may allow particulate to enter the cavity 430, and become captured within the space 432 between the intermediate and distal portions 426, 428.

The use of these latter embodiments may follow the methodology described for the filter element 216 shown in FIGS. 5A–5C. Unlike the filter element 216, however, aspiration may be eliminated or substantially reduced. For example, aspiration may be used to remove relatively large particulate, e.g., that are too large to pass through the intermediate portions 326, 426. Once a procedure is completed, the filter elements 316, 416 may be returned to their elongate configurations and collapsed, trapping the particulate within the spaces 332, 432 within the filter elements 316, 416. The filter elements 316, 416 may then be removed from the vessel, substantially safely removing the captured particulate with them.

In order to program or "teach" a filter element to become biased to or "remember" a predetermined everted configuration, a heat treatment process may be used. When conventional tubular braid material is foreshortened, it naturally expands. If foreshortening is continued, the braid may bunch up, and/or may begin to invert upon itself. Generally, this inverting occurs in a random manner that is generally not repeatable. Thus, such devices are not biased to a predetermined everted configuration, but merely assume an everted state that is difficult to predict each time the device is everted.

In contrast, a filter device in accordance with the present invention preferably becomes everted completely and/or repeatably to assume a predetermined everted configuration having a desired shape. Initially, an elongate tubular mesh may be provided having first and second ends, and first and second portions adjacent the first and second ends, respectively. In a preferred embodiment, a braid of tubular strands may be provided that defines the first and second ends, which may be tapered and/or substantially enclosed. The braid may provide a desired pore size, e.g., size of openings between the strands of the braid, that may prevent particulate larger than the pore size from passing through the openings, as is known to those skilled in the art.

The tubular braid may be physically constructed using multiple braid configurations. Some of the variables involved in forming a tubular braid include: total strand count, number of pics per inch, and weave pattern. Standard braids often use total strand counts in multiples of 8 (i.e. 8, 16, 32, 64, 128, etc), and typically have a weave pattern of "two-over, two-under." Braids may become more flexible when the pic count is increased. As explained above, as a tubular braid is foreshortened from its elongate tubular configuration, the braid expands and ultimately inverts. As the braid is expanded, the density of fibers decreases as the individual strands slide away from each other. Therefore, the desired total strand and pic count may be determined from the desired filter "pore size" in the tubular mesh's largest possible configuration. Any reduction in diameter of the tubular mesh from this position may only reduce the equivalent pore size so that safety of the tubular mesh is maximized.

An exemplary tubular mesh may be a polyester tubular material having a total strand count of sixty four (64) and a pic count of thirty pics per inch (30 pics/in.). These strands may be made from different materials and/or having different geometric sizes. At its maximum diameter of sixteen millimeters (16 mm), the maximum pore size may be approximately 0.75 mm×0.75 mm square. As the tubular mesh is forced to conform to a smaller diameter, e.g., of eight millimeters (8 mm) the pore size may decrease approximately fifty percent (50%). Because the area of a parallelogram is equal to the product of its base and height, as the height of the pores decreases, the area of the pore size decreases by the same factor.

If the desired pore size is smaller than 0.75 mm square, then the pic count and/or the strand count may be increased until a desired pore size is achieved. However, increasing the total strand count may also result in a larger profile of the tubular braid in its relaxed configuration if the diameter of the individual strands is not adjusted accordingly.

Once a desired tubular mesh is selected and formed, the tubular mesh may be shaped into an predetermined everted configuration in which the second portion is disposed concentrically within the first portion. For example, the tubular mesh may be mounted to one or more mandrels having shapes corresponding to the desired everted configuration using methods known to those skilled in the art.

The tubular mesh may be heated to a predetermined temperature for a predetermined time to set the everted configuration or "program" the everted configuration into a "memory" of the tubular mesh material. This may include placing the mandrel and tubular mesh within an oven, autoclave, or other apparatus and/or heating the mandrel itself. After heating is completed, the tubular mesh may be removed from the mandrel and cooled.

The second portion of the tubular mesh may be removed from within the first portion to dispose the tubular mesh in an elongate, generally axial configuration. Preferably, the heat treatment is such that the tubular mesh may maintain the elongate configuration in a relaxed state when free from external forces, rather than automatically everting itself. Alternatively, the filter element may become biased to always return to the everted configuration when in a relaxed state.

In one preferred embodiment, the tubular mesh is formed from plastic, e.g., polyester, nylon, or polyamide and/or metal, e.g., Nitinol or stainless steel, or a combination of metal and polymer. The tubular mesh may be made of filaments having a flat or rectangular cross-section in order to facilitate a minimal profile in the compressed state. The heating step generally involves heating the tubular mesh to between about two hundred and eight hundred degrees Celsius (200–800° C.), preferably at least about four hundred degrees Celsius (400° C.) for between about five and one hundred seconds (5–100 s), and preferably at least about thirty seconds (30 s). These parameters may be adapted to other polymers, using higher/lower temperatures and/or longer/shorter heating times, as will be appreciated by those skilled in the art.

In another preferred embodiment, the tubular mesh may be formed from Nitinol or other shape memory alloy. For such materials, the tubular mesh may be heated to between about 350–525° C. for a predetermined time. Depending upon the apparatus and procedure used to heat the tubular mesh, e.g., using salt pots, sand pots, and ovens, the duration of the heat-treating process may vary. Alternatively, the conditioning of the tubular mesh may be accomplished using physical manipulation, e.g., for annealed materials that are plastically deformable.

The first and second ends of the tubular mesh may be attached to ends of respective guidewires. For example, as described above, concentric guidewires may provided with the distal end of the inner guidewire extending beyond the distal end of the outer guidewire. The first and second ends of the tubular mesh may be attached to the respective ends of the guidewires by adhesive, crimping, soldering, welding, and the like (alone or in combination).

Thus, the first and second guidewires may be movable axially with respect to one another to move the first and second ends towards and away from one another. As described above, the tubular mesh may maintain an elongate configuration in a first relaxed state when the guidewires are free from tension. When the distal ends of the guidewires are directed towards one another, the tubular mesh is everted, causing the tubular mesh to assume the everted configuration programmed into the tubular mesh material. The tubular mesh may maintain the everted configuration until the guidewires are used to return the tubular mesh to the elongate configuration.

In an alternative embodiment, the tubular mesh may provide a structural framework that carries a porous film or skin (not shown). For example, a tubular mesh may be formed using the methods described above, e.g., from metals and/or polymers. The tubular mesh may include openings that are relatively large compared to a desired pore size for a filter element. A porous skin may be formed on or within the tubular mesh to provide a desired pore size that may be substantially smaller than the openings in the tubular mesh. Preferably, the porous skin is substantially flexible, e.g., to accommodate movement of the tubular mesh between tubular and everted configurations.

For example, the tubular mesh may be dipped one or more times into a polyester or other heated or uncured elastomer, causing the elastomer to extend across or otherwise fill the openings between the strands in the tubular mesh. Once the elastomer is cooled and/or otherwise cured into a substantially continuous film of a desired thickness, holes may be formed in the film, e.g., by laser drilling and the like, to provide a desired pore size. Alternatively, a porous film or other skin may be made that already includes a plurality of holes providing a desired pore size. The porous film may be attached to the tubular mesh, e.g., along an outer or inner surface thereof, using an adhesive, sonic welding, and the like.

Figure 8:
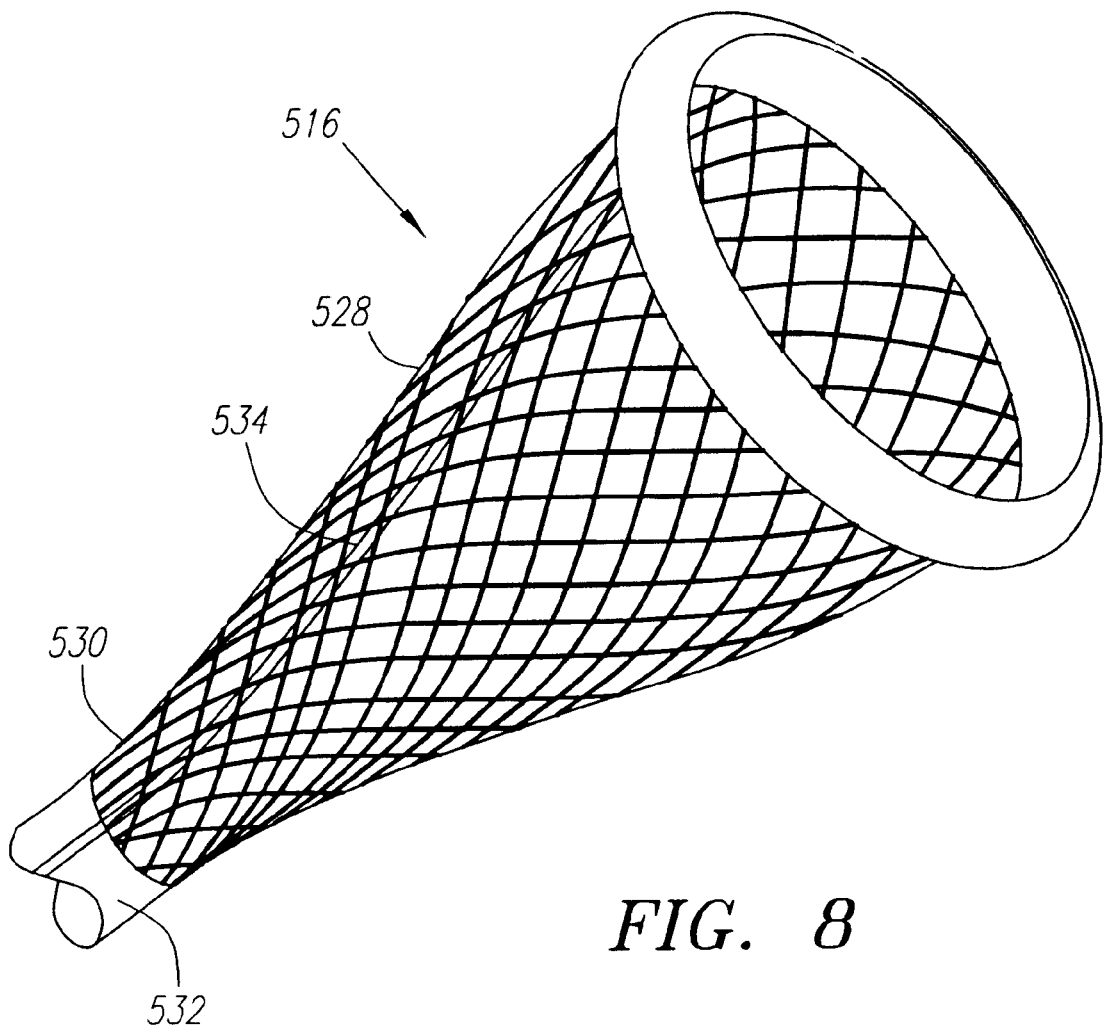
FIG. 8 is a perspective view of another embodiment of a filter element for capturing particulate, in accordance with the present invention.

Turning to FIG. 8, another embodiment of a filter element 516 is shown that may be used in conjunction with a device, such as the shearing apparatus described above (not shown). Generally, the filter element 516 includes an expandable collar 526 and a filter mesh 528 extending from the collar 526. Preferably, the filter mesh 528, which may be formed similar to the filter elements described above, tapers from the collar 526 to a substantially closed end 530. An elongate member, e.g., a tubular element 532, extends from the closed end 530 of the filter mesh 528. Alternatively, an elongate member, e.g., a guidewire or a tubular member, may be connected directly to the collar 526.

Preferably, the collar 526 is an inflatable ring that may be filled with fluid, such as saline, to expand the collar 526 from a collapsed state to one or more expanded states. An inflation lumen 534 extends from the collar 526, e.g., along the filter mesh 528 to the tubular element 532. The collar 526 may be an elastic balloon formed, for example, from C-Flex, silicone, poly-isoprene, latex, and the like,] that is sufficiently flexible and resilient to allow expansion to one or more expanded states. Alternatively, the collar 526 may be formed from substantially inelastic material, e.g. PET, that may expand to a predetermined size.

During use, the collar 526 may be deflated, and the filter mesh 528 collapsed, e.g., by compressing or twisting the collar 526 relative to the tubular element 532. A sheath or other device (not shown) may be advanced over the filter element 416 to constrain and/or protect the filter element 416. The filter element 416 may be advanced into a blood vessel or other body lumen, e.g., to a location downstream of a treatment site, similar to the embodiments described above.

The collar 526 may then be expanded, e.g., by delivering fluid through the tubular element 532, through the inflation lumen 534 and into an interior of the collar 526. Preferably, the collar 526 is expanded to substantially engage a wall of the vessel, thereby requiring fluid flowing past the location to pass through the filter mesh 528. A procedure may be performed, and particulate may be captured within the filter mesh 528. Aspiration may be performed, if desired, to remove particulate captured by the filter mesh 528.

Upon completing the procedure, the collar 526 may be deflated, and the filter element 516 removed, using procedures similar to those described above. If aspiration is not used (or if particulate remains within the filter mesh 528, it may be desirable to provide the collar 526 from resilient material that is biased to close, thereby trapping particulate within the filter mesh 528 before removing the filter element 516.

Figure 9:
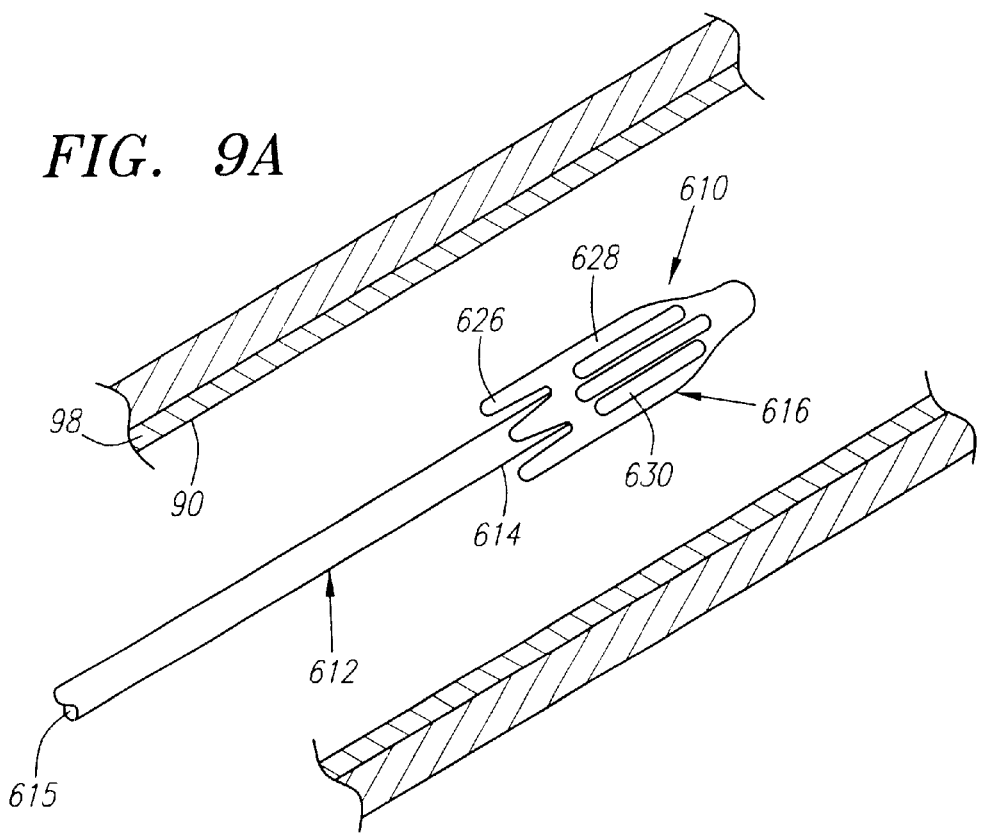
FIGS. 9A and 9B are cross-sectional views of another preferred embodiment of an expandable filter element being used to capture particulate within a blood vessel, in accordance with the present invention.
Figure 10:
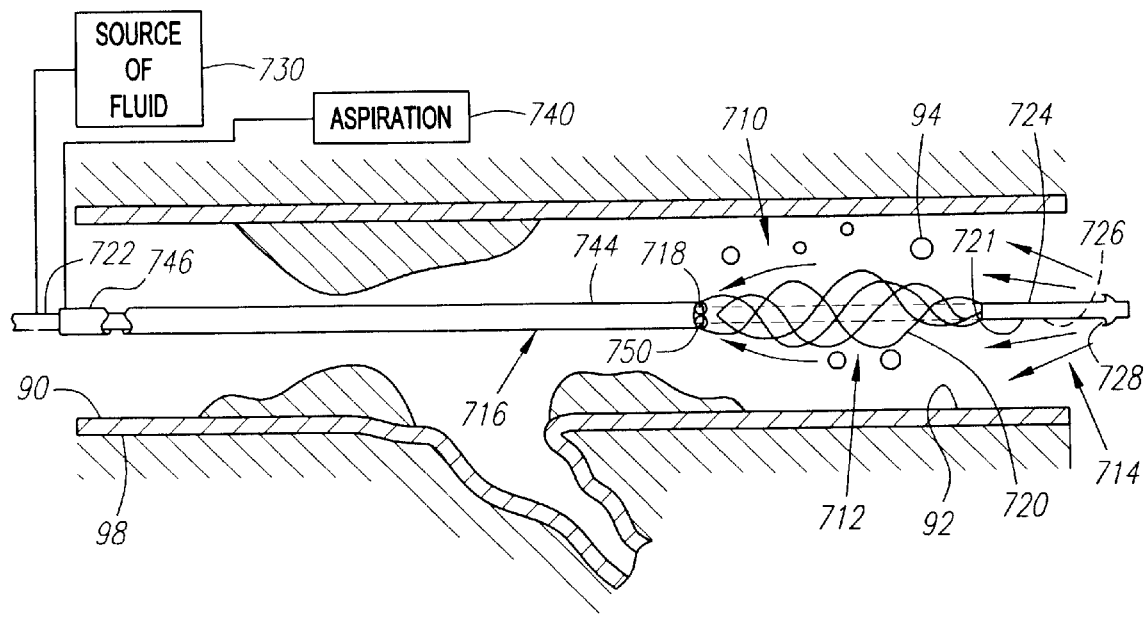
FIG. 10 is a cross-sectional view of a blood vessel, showing an apparatus for capturing particulate during a maceration procedure, in accordance with the present invention.

Turning to FIGS. 9A and 9B, yet another preferred embodiment of an apparatus 610 is shown for capturing particulate within a blood vessel 90. Generally, the apparatus 610 includes an elongate tubular member 612 having a distal end 614 with an expandable filter element 616 disposed on the distal end 614. The tubular member 612 includes an inflation lumen 615 communicating with an interior of the filter element 616. The tubular member may also include a guidewire lumen (not shown) to facilitate advancing the apparatus 610 over a guidewire (also not shown) into the vessel 90.

The filter element 616 includes one or more annular rings or collar 626 and a gridwork of elements 628 disposed across an interior of the collars 626 to provide a plurality of openings 630 in the filter element 616. In a preferred embodiment, the elements 628 are spokes extending from a central hub 632 radially outward to the collars 626, as best seen in FIG. 9B. At least one, and preferably all, of the elements 628 are tubular and include an interior in communication with an interior of the collar 626. The interior of the collar 626 and/or the elements 628 also communicate with the inflation lumen 615 in the tubular member 612, e.g., via the hub 632.

To form the filter element 616, a pair of flat sheets (not shown) of flexible, and preferably elastic material, e.g., C-Flex, silicone, poly-isoprene, latex, and the like, are provided that overly each other. Preferably, the sheets are generally circular and have a diameter corresponding to a desired expanded diameter of the filter element 616, e.g., between about one and forty millimeters (1–40 mm). A plurality of holes are created in the sheets that correspond to the openings 630 in the filter element 616 to provide the collar 626 and the gridwork of elements or spokes 628. Edges of the remaining material of the sheets are attached to one another, thereby defining a space between the sheets that is corresponds to the interior of the collar 626 and the elements 628. In a preferred embodiment, the holes are formed by laser cutting and the like, which may simultaneously seal the edges as the holes are formed. Alternatively, the holes may be formed, e.g., by mechanical cutting, chemical etching, and the like, and then the edges of the sheets may be attached, e.g., using adhesives, sonic welding, and the like. Alternatively, the two sheets may have a cylindrical, triangular, conical, or other shape that may be rolled or otherwise formed into a desired filter element.

The tubular member 612 may then be attached to the resulting structure, e.g., at the central hub 630. The inflation lumen of 615 the tubular member 612 may be coupled to the interior of the filter element 616, e.g., by connecting a secondary tube (not shown) between the filter element 616 and the tubular member 612. Alternatively, an opening (not shown) may be created in one of the sheets, e.g., at the central hub 630, and the tubular member 612 may be connected to the filter element 616 around the hole, thereby coupling the lumen 615 to the interior of the filter element 616.

With the filter element 616 deflated, it may be wrapped over the distal end 614 of the tubular member 612, e.g., by simply lying the filter element 616 over the distal end 614, and/or by twisting the filter element 616 relative to the tubular member 612. If desired, a sheath or other device (not shown) may be advanced over the collapsed filter element 616 to constrain and/or protect the filter element 616 during delivery into a patient's body.

As shown in FIG. 9A, similar to the embodiments described above, the filter element 616, in its collapsed state, may be introduced into a patient's vasculature and advanced into a blood vessel 90 at a location downstream from a treatment site (not shown). The filter element 616 may be deployed (e.g., by retracting an overlying sheath, not shown) and fluid may be introduced via the lumen 615 into the interior of the filter element 616 to expand the filter element 616. As the filter element 616 is inflated, the collar 626 expands to substantially engage the wall 98 of the vessel 90 and the elements 628 expand to provide a plurality of openings 630 through which fluid may flow. Preferably, the filter element 616 is formed from material that is sufficiently elastic such that the collar 626 may be expanded to one of a plurality of expanded states, e.g., to accommodate a range of size of vessels. The elasticity of the filter element material may be limited to prevent the openings 630 from expanded beyond a desired maximum size.

A procedure may be performed upstream from the filter element 616, which may release particulate 94 that may travel downstream and become captured by the filter element 616, as shown in FIG. 9B. Aspiration may be used one or more times during the procedure to remove the captured particulate, e.g., by advancing an aspirating catheter (not shown) over the tubular member 612. Upon completing the procedure, the filter element 616 may be deflated and removed from the vessel 90.

In addition, or alternatively, the filter element 616 may be biased to fold proximally to the collapsed state shown in FIG. 9A. For example, upon completing the procedure, the filter element 616 may be deflated, causing the filter element 616 to fold proximally and trap particulate between the filter element 616 and the tubular member 612.

Turning to FIGS. 10 and 11A–11D, another embodiment of an apparatus 710 is shown that may be used to remove particulate from within a blood vessel 90 or other body lumen. Generally, the apparatus 710 includes a treatment device 712, a backflow device 714, and an aspirating device 716. The treatment device 712 includes a treatment element on its distal end 718. In the embodiment shown, the treatment element is a shearing basket 720, such as that disclosed in the applications incorporated above. Alternatively, the treatment element may include an angioplasty balloon and/or a stent (not shown), and the like.

The backflow device 714 includes a tubular member 721 including a proximal end 722, a distal end 724, and a lumen 726 extending between the proximal and distal ends 722, 724. The backflow device 714 is cooperatively associated with the treatment device 712. In a preferred embodiment, the backflow device 714 is slidably disposed within a lumen (not shown) of the treatment device 714 such that a distal end 724 of the backflow device 714 may be disposed distally beyond the distal end 718 of the treatment device 712. Alternatively, the backflow device 714 may be deliverable into a patient independently from the treatment device 712 (not shown).

The backflow device 714 includes one or more openings 728 in its distal end 724 that communicate with the lumen 726 extending proximally from the distal end 718 to a proximal end 722. A source of fluid 730 may be coupled to the proximal end 722 of the tubular member 721 for delivering fluid at a desired pressure and flow rate via the lumen 726 to the openings 728. Preferably, the openings 728 have a predetermined configuration for causing fluid flowing from the openings 728 to be directed proximally, i.e., towards the proximal end 822 of the backflow device 714.

Figure 11A:
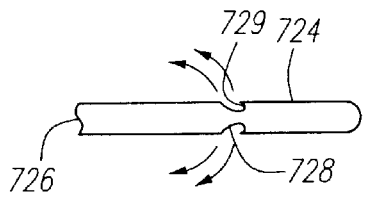
FIGS. 11A–11D show alternative embodiments of devices that may create backflow for use with the apparatus of FIG. 10.
Figure 11B:
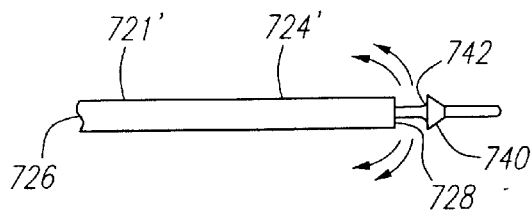
Figure 11C:
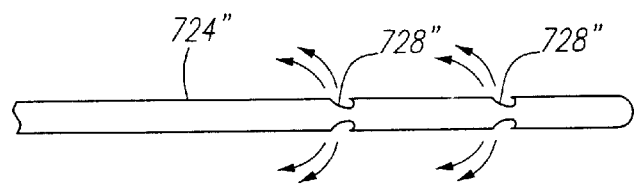
Figure 11D:
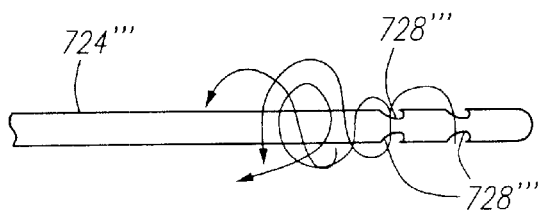

Turning to FIG. 11A, a first embodiment of a distal end 724 of the backflow device 714 is shown that includes openings 728 shaped to create an umbrella-shaped flow pattern. This may be accomplished by providing ramped surfaces 729 within the distal end 724 of the tubular member 721. Alternatively, as shown in FIG. 11B, a deflector member 740 may be provided on the distal end 724' of the tubular member 721'. The deflector member 740 may include proximally oriented ramped surfaces 742 for deflecting fluid flowing from an outlet 728' to create an umbrella-shaped flow pattern. Alternatively, the deflector member 740 may have a configuration for creating an asymmetrical flow pattern, e.g., including one or more radial zones of proximal flow. In a further alternative, shown in FIG. 11C, multiple banks of openings 728" may be provided along the distal end 724" of the tubular member 721" to enhance the proximal flow pattern desired. In yet a further alternative, shown in FIG. 11D, openings 728'" may be provided that create a proximal vortex flow pattern.

Returning to FIG. 10, the aspirating device 716 may be an aspirating catheter including a distal end 744 that may be advanced into the vessel 90, a proximal end 746 that may remain outside the patient's body, and a lumen 750 extending therebetween. A source of vacuum 748 is coupled to the proximal end 746 for creating a vacuum at the distal end 744. In a preferred embodiment, the aspirating device 716 may be advanced over the treatment device 712. Alternatively, the aspirating device 716 may be advanced over the backflow device 714 (e.g., if delivered separately from the treatment device 712) or the aspirating device 716 may be introduced independently from the other devices.

During use, the apparatus 710 is introduced into a vessel 90, e.g., from a location upstream or downstream from the treatment site 92, similar to the previous embodiments. The backflow device 714 is positioned downstream from the treatment element 720 and/or the treatment site 92, while the distal end 744 of the aspirating catheter 716 is disposed upstream from the backflow device 714. Fluid may be introduced through the lumen 726 of the backflow device 714 to create a retrograde flow pattern out the openings 728. To further enhance creating retrograde flow, a vacuum may be generated at the distal end 744 of the aspirating catheter 716 to create a net flow at the treatment site 92 that is retrograde, and preferably into the lumen 750 of the aspirating catheter 716.

A procedure may be performed at the treatment site 92, which may involve releasing particulate 94 from the wall 98 of the vessel 90. Because of the retrograde flow created by the openings 728 in the backflow device 714, particulate may not pass distally beyond the backflow device 714 and travel downstream. In addition, because of the vacuum created by the aspirating catheter 716, the particulate 94 may be pulled into lumen 750 of the aspirating catheter 716, and removed from the patient's vasculature. Upon completing the procedure, use of the backflow device 714 and the aspirating catheter 716 may be discontinued, and the apparatus 710 may be removed from the vessel 90.

Figure 12:
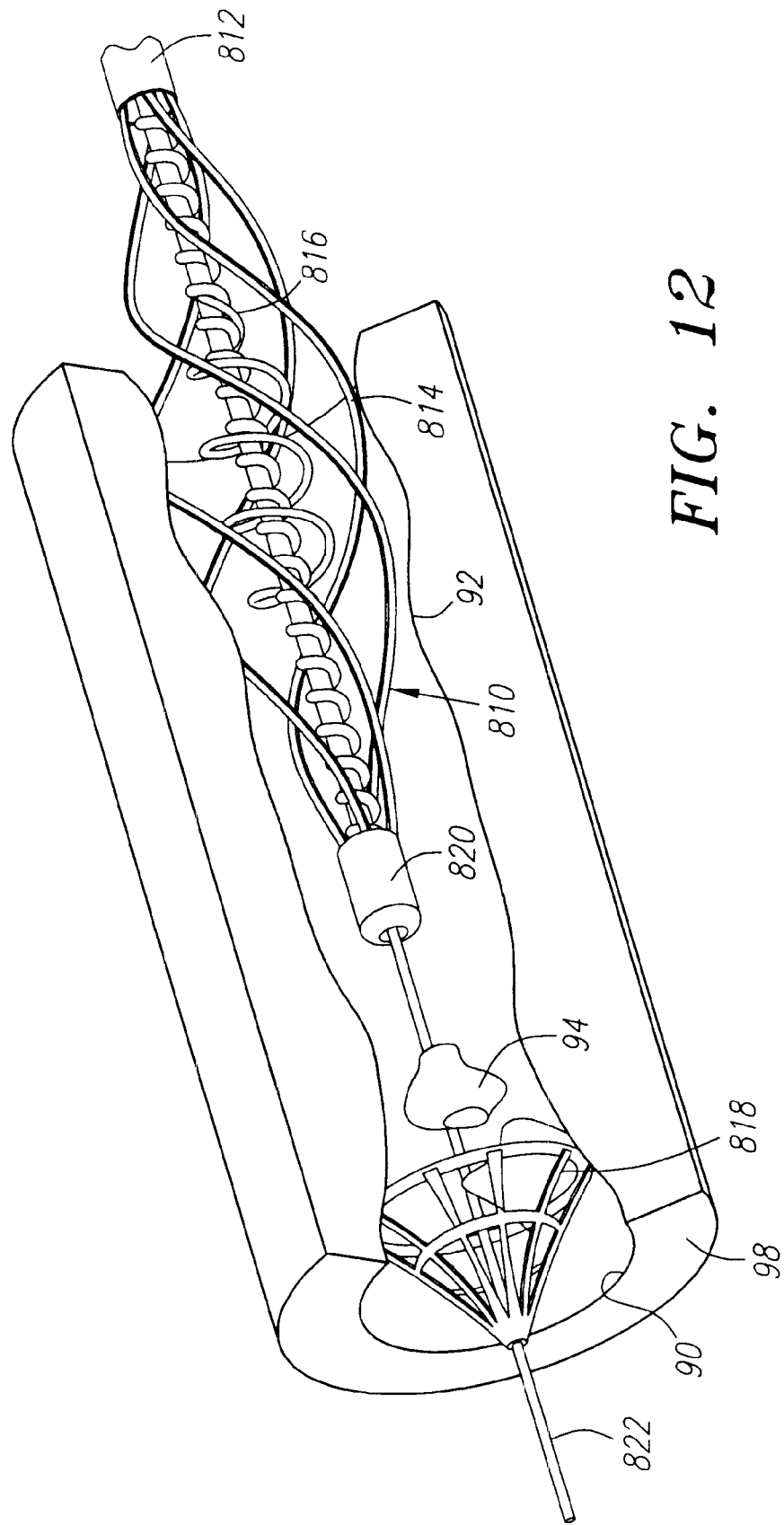
FIG. 12 is a perspective view of another embodiment of an apparatus for capturing particulate released during a thrombectomy procedure.

Turning to FIG. 12, yet another embodiment of an apparatus 810 is shown that may be used to perform a procedure, e.g., a thrombectomy, within a blood vessel 90 or other body lumen. Generally, the apparatus 810 is an elongate member 812, preferably a tubular member, including a shearing member 814, a mechanically aspirating pump 816, and a filter element 818 on its distal end.

The mechanically aspirating pump 816 includes a helical screw that may be rotated within the shearing member 814, e.g., to generate a vacuum or otherwise remove particulate at the distal tip 820. Additional information on the structure and operation of the mechanically aspirating pump 816 may be found in co-pending application Ser. No. 09/454,517, filed Dec. 6, 1999 and in PCT Publication No. WO 01/19, 444, published Mar. 22, 2001, the disclosures of which are expressly incorporated herein by reference.

The filter element 818 may be an expandable frame or mesh, such as that described above. The filter element 818 may be inflated to expand, as described above, or may be mechanically expandable, e.g., by an actuator at a proximal end (not shown) of the elongate member 812. In a further alternative, the filter element 818 may be self-expanding.

During use, the apparatus 810 may be introduced into a patient, and advanced into the blood vessel 90 until the shearing member 814 is disposed adjacent a treatment site 92. The filter element 818 may be disposed within the vessel 90 downstream from the treatment site 92, e.g., by advancing a guidewire 822 carrying the filter element 818 from within the elongate member 812. The filter element 818 may be expanded across the lumen 90, e.g., to substantially engage the wall 98.

A procedure may be performed at the treatment site 92, e.g., a thrombectomy, that may release particulate 94 into the vessel 90. For example, the shearing member 814 may be rotated or otherwise activated to shear thrombus or other tissue from the wall 98 of the vessel 90. Alternatively, the shearing member 814 may be replaced with other therapeutic or diagnostic devices. For example, a device may be provided to perform vibrational and/or mechanical dissolution of thrombus or other material on the wall 98. U.S. Pat. Nos. 5,380,273, 5,498,236, and 5,713,848, and PCT Publication No. WO 96/39,955 disclose devices that may be incorporated into the apparatus 810.

The filter element 818 may capture particulate 94 released during the procedure, similar to the embodiments described above. At one or more times during the procedure and/or upon completing the procedure, the distal tip 820 may be advanced towards the filter element 818 to aspirate particulate 94 captured by the filter element 818 using the mechanically aspirating pump 816. Alternatively, an aspirating catheter (not shown) may be used instead of or in addition to the mechanically aspirating pump 816.

Upon completing the procedure, the filter element 818 may be collapsed and/or returned into the elongate member 812 and then the apparatus 810 may be withdrawn from the vessel 90, moved to another treatment site (not shown), and/or removed from the patient.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for capturing particulate within a body lumen of a patient, comprising:
    a first elongate member comprising a distal portion having a size for introduction into a body lumen and defining a longitudinal axis; and
    a tubular filter element having first and second ends adjacent first and second respective portions of the filter element, the first end being substantially fixed to the distal portion of the first elongate member, the second end being movable axially with respect to the distal portion of the first elongate member towards the first end to evert the filter element, wherein the filter element is biased to assume a predetermined open configuration when the second portion of the filter element is everted substantially within the first portion of the filter element.

2. The apparatus of claim 1, wherein the filter element comprises an intermediate annular portion between the first and second portions, the intermediate annular portion being biased to expand when the filter element assumes the everted configuration, the intermediate annular portion thereby defining an outer-most edge of the filter element adapted to engage the wall of a blood vessel.

3. The apparatus of claim 1, further comprising a second elongate member comprising a distal portion to which the second end of the filter element is fixed, the second elongate member being slidable along the first elongate member for moving the first and second ends of the filter element towards one another to cause the filter element to evert.

4. The apparatus of claim 3, wherein the second elongate member comprises a lumen through which the first elongate member is slidably received.

5. The apparatus of claim 1, further comprising an aspirating element having an inlet that may be disposed within an interior of the filter element in the everted configuration.

6. The apparatus of claim 5, wherein the aspirating element comprises a catheter for removing particulate captured by the filter element.

7. The apparatus of claim 6, where in the catheter comprises a thrombectomy catheter including a mechanically aspirating pump for removing particulate captured by the filter element.

8. The apparatus of claim 1, wherein the filter element defines a space between the first and second portions in the predetermined configuration, and wherein the first portion includes pores therein that are substantially smaller than pores in the second portion.

9. The apparatus of claim 8, wherein the filter element further comprises one or more struts extending from the second portion of the filter element to a distal end of a second elongate member slidably disposed on the first elongate member.

10. The apparatus of claim 1, wherein the filter element is biased to assume an expanded tubular configuration when the second portion of the filter element is removed from within the first portion.

* * * * *